(12) United States Patent
Ying et al.

(10) Patent No.: US 7,692,650 B2
(45) Date of Patent: Apr. 6, 2010

(54) METHOD OF AND SYSTEM FOR 3D DISPLAY OF MULTI-ENERGY COMPUTED TOMOGRAPHY IMAGES

(75) Inventors: Zhengrong Ying, Wakefield, MA (US); Matthew Hirsch, Cambridge, MA (US); Purvin Desai, Waltham, MA (US); Kyle Guilbert, Malden, MA (US); Sergey Simanovsky, Brookline, MA (US); Carl R. Crawford, Brookline, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 11/142,216

(22) Filed: Jun. 1, 2005

(65) Prior Publication Data

US 2006/0274066 A1 Dec. 7, 2006

(51) Int. Cl.
*G06T 17/00* (2006.01)

(52) U.S. Cl. ...................................................... 345/424
(58) Field of Classification Search .................. 345/424
See application file for complete search history.

(56) References Cited

U.S. PATENT DOCUMENTS

| | | | | |
|---|---|---|---|---|
| 4,029,963 A | 6/1977 | Alvarez et al. | ............... | 250/360 |
| 4,759,047 A | 7/1988 | Donges et al. | ................. | 378/57 |
| 4,884,289 A | 11/1989 | Glockmann et al. | ............ | 378/57 |
| 5,132,988 A | 7/1992 | Fisher et al. | .................... | 375/14 |
| 5,132,998 A | 7/1992 | Tsutsui et al. | .................. | 378/99 |
| 5,182,764 A | 1/1993 | Peschmann et al. | ............ | 378/57 |
| 5,247,561 A | 9/1993 | Kotowski | ....................... | 378/87 |
| 5,319,547 A | 6/1994 | Krug et al. | ................... | 364/409 |
| 5,367,552 A * | 11/1994 | Peschmann | .................... | 378/57 |
| 5,473,657 A | 12/1995 | McKenna | ....................... | 378/4 |
| 5,490,218 A | 2/1996 | Krug et al. | .................... | 382/100 |
| 5,661,774 A * | 8/1997 | Gordon et al. | .............. | 378/101 |
| 6,008,813 A * | 12/1999 | Lauer et al. | .................. | 345/424 |
| 6,026,171 A * | 2/2000 | Hiraoglu et al. | ............. | 382/100 |
| 6,091,795 A | 7/2000 | Schafer et al. | ................. | 378/19 |
| 6,198,797 B1 * | 3/2001 | Majima et al. | ................. | 378/98 |
| 6,483,507 B2 * | 11/2002 | Osborne et al. | ............. | 345/419 |
| 6,554,430 B2 | 4/2003 | Dorval et al. | ................... | 353/7 |
| 6,574,302 B2 * | 6/2003 | Adriaansz | ..................... | 378/54 |

(Continued)

FOREIGN PATENT DOCUMENTS

DE 3150306 A1 6/1983

OTHER PUBLICATIONS

The DICOM Standard, Apr. 2002, http://www.psyc.nott.ac.uk/staff/cr1/dicom.html, pp. 1-6.*

(Continued)

*Primary Examiner*—Ulka Chauhan
*Assistant Examiner*—Said Broome
(74) *Attorney, Agent, or Firm*—McDermott Will & Emery LLP (57) ABSTRACT

A method of and a system for displaying volumetric multi-energy CT images are disclosed, wherein a CT image, a Z image, and a label image from an automatic explosive detection are provided, are disclosed. The method comprises generating an index image through a nonlinear transformation of the CT image, the Z image, and the label image, rotating and coloring the index image as desired, and rendering and displaying the rotated and colored image.

22 Claims, 6 Drawing Sheets

U.S. PATENT DOCUMENTS 6,618,466 B1 * 9/2003 Ning .......................... 378/62
6,909,792 B1 * 6/2005 Carrott et al. ............... 382/128
2004/0252873 A1 * 12/2004 Avinash et al. ............. 382/132

OTHER PUBLICATIONS

Alvarez, R. E., et al., "Energy-selective Reconstruction in X-ray Computerized Tomography", Phys. Med. Biol. 1976, vol. 21, No. 5, 733-744.

Lehmann, L. A., et al., "Generalized Image Combinations in Dual KVP Digital Radiography", Med. Phys. 8, 659-667 (1981).

Chuang K., et al., "A Fast Dual-Energy Computational Method Using Isotransmission Lines and Tables", Med. Phys. 14, 186-192 (1987).

Rezk-Salama, C., "Volume Rendering Techniques For General Purpose Graphics Hardware", University of Erlangen, Dec. 2001.

* cited by examiner

METHOD OF AND SYSTEM FOR 3D DISPLAY OF MULTI-ENERGY COMPUTED TOMOGRAPHY IMAGES

RELATED APPLICATIONS

This patent application and/or patents are related to the following co-pending U.S. applications and/or issued U.S. patents, of the assignee as the present application, the contents of which are incorporated herein in their entirety by reference:

"Nutating Slice CT Image Reconstruction Apparatus and Method," invented by Gregory L. Larson, et al., U.S. application Ser. No. 08/831,558, filed on Apr. 9, 1997, now U.S. Pat. No. 5,802,134, issued on Sep. 1, 1998;

"Computed Tomography Scanner Drive System and Bearing," invented by Andrew P. Tybinkowski, et al., U.S. application Ser. No. 08/948,930, filed on Oct. 10, 1997, now U.S. Pat. No. 5,982,844, issued on Nov. 9, 1999;

"Air Calibration Scan for Computed Tomography Scanner with Obstructing Objects," invented by David A. Schafer, et al., U.S. application Ser. No. 08/948,937, filed on Oct. 10, 1997, now U.S. Pat. No. 5,949,842, issued on Sep. 7, 1999;

"Computed Tomography Scanning Apparatus and Method With Temperature Compensation for Dark Current Offsets," invented by Christopher C. Ruth, et al., U.S. application Ser. No. 08/948,928, filed on Oct. 10, 1997, now U.S. Pat. No. 5,970,113, issued on Oct. 19, 1999;

"Computed Tomography Scanning Target Detection Using Non-Parallel Slices," invented by Christopher C. Ruth, et al., U.S. application Ser. No. 08/948,491, filed on Oct. 10, 1997, now U.S. Pat. No. 5,909,477, issued on Jun. 1, 1999;

"Computed Tomography Scanning Target Detection Using Target Surface Normals," invented by Christopher C. Ruth, et al., U.S. application Ser. No. 08/948,929, filed on Oct. 10, 1997, now U.S. Pat. No. 5,901,198, issued on May 4, 1999;

"Parallel Processing Architecture for Computed Tomography Scanning System Using Non-Parallel Slices," invented by Christopher C. Ruth, et al., U.S. application Ser. No. 08/948,697, filed on Oct. 10, 1997, U.S. Pat. No. 5,887,047, issued on Mar. 23, 1999;

"Computed Tomography Scanning Apparatus and Method For Generating Parallel Projections Using Non-Parallel Slice Data," invented by Christopher C. Ruth, et al., U.S. application Ser. No. 08/948,492, filed on Oct. 10, 1997, now U.S. Pat. No. 5,881,122, issued on Mar. 9, 1999;

"Computed Tomography Scanning Apparatus and Method Using Adaptive Reconstruction Window," invented by Bernard M. Gordon, et al., U.S. application Ser. No. 08/949,127, filed on Oct. 10, 1997, now U.S. Pat. No. 6,256,404, issued on Jul. 3, 2001;

"Area Detector Array for Computed Tomography Scanning System," invented by David A Schafer, et al., U.S. application Ser. No. 08/948,450, filed on Oct. 10, 1997, now U.S. Pat. No. 6,091,795, issued on July 18, 2000;

"Closed Loop Air Conditioning System for a Computed Tomography Scanner," invented by Eric Bailey, et al., U.S. application Ser. No. 08/948,692, filed on Oct. 10, 1997, now U.S. Pat. No. 5,982,843, issued on Nov. 9, 1999;

"Measurement and Control System for Controlling System Functions as a Function of Rotational Parameters of a Rotating Device," invented by Geoffrey A. Legg, et al., U.S. application Ser. No. 08/948,493, filed on Oct. 10, 1997, now U.S. Pat. No. 5,932,874, issued on Aug. 3, 1999;

"Rotary Energy Shield for Computed Tomography Scanner," invented by Andrew P. Tybinkowski, et al., U.S. application Ser. No. 08/948,698, filed on Oct. 10, 1997, now U.S. Pat. No. 5,937,028, issued on Aug. 10, 1999;

"Apparatus and Method for Detecting Sheet Objects in Computed Tomography Data," invented by Muzaffer Hiraoglu, et al., U.S. application Ser. No. 09/022,189, filed on Feb. 11, 1998, now U.S. Pat. No. 6,111,974, issued on Aug. 29, 2000;

"Apparatus and Method for Eroding Objects in Computed Tomography Data," invented by Sergey Simanovsky, et al., U.S. application Ser. No. 09/021,781, filed on Feb. 11, 1998, now U.S. Pat. No. 6,075,871, issued on Jun. 13, 2000;

"Apparatus and Method for Combining Related Objects in Computed Tomography Data," invented by Ibrahim M. Bechwati, et al., U.S. application Ser. No. 09/022,060, filed on Feb. 11, 1998, now U.S. Pat. No. 6,128,365, issued on Oct. 3, 2000;

"Apparatus and Method for Detecting Sheet Objects in Computed Tomography Data," invented by Sergey Simanovsky, et al., U.S. application Ser. No. 09/022,165, filed on Feb. 11, 1998, now U.S. Pat. No. 6,025,143, issued on Feb. 15, 2000;

"Apparatus and Method for Classifying Objects in Computed Tomography Data Using Density Dependent Mass Thresholds," invented by Ibrahim M. Bechwati, et al., U.S. application Ser. No. 09/021,782, filed on Feb. 11, 1998, now U.S. Pat. No. 6,076,400, issued on Jun. 20, 2000;

"Apparatus and Method for Correcting Object Density in Computed Tomography Data," invented by Ibrahim M. Bechwati, et al., U.S. application Ser. No. 09/022,354, filed on Feb. 11, 1998, now U.S. Pat. No. 6,108,396, issued on Aug. 22, 2000;

"Apparatus and Method for Density Discrimination of Objects in Computed Tomography Data Using Multiple Density Ranges," invented by Sergey Simanovsky, et al., U.S. application Ser. No. 09/021,889, filed on Feb. 11, 1998, now U.S. Pat. No. 6,078,642, issued on Jun. 20, 2000;

"Apparatus and Method for Detection of Liquids in Computed Tomography Data," invented by Muzaffer Hiraoglu, et al., U.S. application Ser. No. 09/022,064, filed on Feb. 11, 1998, now U.S. Pat. No. 6,026,171, issued on Feb. 15, 2000;

"Apparatus and Method for Optimizing Detection of Objects in Computed Tomography Data," invented by Muzaffer Hiraoglu, et al., U.S. application Ser. No. 09/022,062, filed on Feb. 11, 1998, now U.S. Pat. No. 6,272,230, issued on August 7, 2001;

"Multiple-Stage Apparatus and Method for Detecting Objects in Computed Tomography Data," invented by Muzaffer Hiraoglu, et al., U.S. application Ser. No. 09/022,164, filed on Feb. 11, 1998, now U.S. Pat. No. 6,035,014, issued on Mar. 7, 2000;

"Apparatus and Method for Detecting Objects in Computed Tomography Data Using Erosion and Dilation of Objects," invented by Sergey Simanovsky, et al., U.S. application Ser. No. 09/022,204, filed on Feb. 11, 1998, now U.S. Pat. No. 6,067,366, issued on May 23, 2000;

"Apparatus and Method for Classifying Objects in Computed Tomography Data Using Density Dependent Mass Thresholds," invented by Ibrahim M. Bechwati, et al., U.S. application Ser. No. 09/021,782, filed on Feb. 11, 1998, now U.S. Pat. No. 6,076,400, issued on Jun. 20, 2000;

"Apparatus and Method for Detecting Concealed Objects in Computed Tomography Data," invented by Sergey Simanovsky, et al., U.S. application Ser. No. 09/228,380, filed on Jan. 12, 1999, now U.S. Pat. No. 6,195,444, issued on Feb. 27, 2001;

"Apparatus and Method for Optimizing Detection of Objects in Computed Tomography Data," invented by Muzaffer Hiraoglu, et al., U.S. application Ser. No. 09/022,062, filed on Feb. 11, 1998, now U.S. Pat. No. 6,272,230, issued on Aug. 7, 2001;

"Computed Tomography Apparatus and Method for Classifying Objects," invented by Sergey Simanovsky, et al., U.S. application Ser. No. 09/022,059, filed on Feb. 11, 1998, now U.S. Pat. No. 6,317,509, issued on Nov. 23, 2001;

"Apparatus and method for processing object data in computed tomography data using object projections," invented by Carl R. Crawford, et al, U.S. application Ser. No. 09/228379, filed on Jan. 12, 1999, now U.S. Pat. No. 6,345,113, issued on Feb. 5, 2002;

"Apparatus and method for detecting concealed objects in computed tomography data," invented by Sergey Simanovsky, et al., U.S. application Ser. No. 09/228,380, filed on Jan. 12, 1999, now U.S. Pat. No. 6,195,444, issued on Feb. 27, 2001;

"Method of and system for correcting scatter in a computed tomography scanner," invented by Ibrahim M. Bechwati, et al, U.S. application Ser. No. 10/121,466, filed on Apr. 11, 2002, now U.S. Pat. No. 6,687,326, issued on Feb. 3, 2004;

"Method of and system for reducing metal artifacts in images generated by x-ray scanning devices," invented by Ram Naidu, et al, U.S. application Ser. No. 10/171,116, filed on Jun. 13, 2002, now U.S. Pat. No. 6,721,387, issued on Apr. 13, 2004;

"Method and apparatus for stabilizing the measurement of CT numbers," invented by John M. Dobbs, U.S. application Ser. No. 09/982,192, filed on Oct. 18, 2001, now U.S. Pat. No. 6,748,043, issued on Jun. 8, 2004;

"Method and apparatus for automatic image quality assessment," invented by Seemeen Karimi, et al, U.S. application Ser. No. 09/842,075, filed on Apr. 25, 2001, now U.S. Pat. No. 6,813,374, issued on Nov. 2, 2004;

"Decomposition of Multi-Energy Scan Projections using Multi-Step Fitting," invented by Ram Naidu, et al, U.S. application Ser. No. 10/611,572, filed on Jul. 1, 2003;

"Method of and system for detecting threat objects using computed tomography images," invented by Zhengrong Ying, et al, U.S. application Ser. No. 10/831,909, filed on Apr. 26, 2004;

"Method of and system for computing effective atomic number image in multi-energy computed tomography," invented by Zhengrong Ying, et al, U.S. application Ser. No. 10/850,910, filed on May 21, 2004;

"Method of and system for adaptive scatter correction in multi-energy computed tomography," invented by Zhengrong Ying, et al, U.S. application Ser. No. 10/853,942, filed on May 26, 2004;

"Method of and system for destreaking the photoelectric image in multi-energy computed tomography," invented by Zhengrong Ying, et al, U.S. application Ser. No. 10/860,984, filed on Jun. 4, 2004;

"Method of and system for extracting 3D bag images from continuously reconstructed 2D image slices in computed tomography," invented by Zhengrong Ying, et al, U.S. application Ser. No. 10/864,619, filed on Jun. 9, 2004;

"Method of and system for sharp object detection using computed tomography images," invented by Gregory L. Larson, et. al., U.S. application Ser. No. 10/883,199, filed on Jul. 1, 2004;

"Method of and system for X-ray spectral correction in multi-energy computed tomography," invented by Ram Naidu, et. al., U.S. application Ser. No. 10/899,775, filed on Jul. 17, 2004;

"Method of and system for detecting anomalies in projection images generated by computed tomography scanners," invented by Anton Deykoon, et. al., U.S. application Ser. No. 10/920,635, filed on Aug. 18, 2004;

"Method of and system for stabilizing high voltage power supply voltages in multi-energy computed tomography," invented by Ram Naidu, et. al., U.S. application Ser. No. 10/958,713, filed on Oct. 5, 2004;

FIELD OF THE DISCLOSURE

The present disclosure relates to methods of and systems for processing images generated by computed tomography scanners, and more particularly to a method of and a system for displaying 3D volumetric images generated by explosive detection systems using multi-energy computed tomography scanners.

BACKGROUND OF THE DISCLOSURE

Various X-ray baggage scanning systems are known for detecting the presence of explosives and other prohibited items in baggage, or luggage, prior to loading the baggage onto a commercial aircraft. A common technique of measuring a material's density is to expose the material to X-rays and to measure the amount of radiation absorbed by the material, the absorption being indicative of the density. Since many explosive materials may be characterized by a range of densities differentiable from that of other items typically found in baggage, explosives are generally amenable to detection by X-ray equipment.

Most X-ray baggage scanning systems in use today are of the "line scanner" type and include a stationary X-ray source, a stationary linear detector array, and a conveyor belt for transporting baggage between the source and detector array as the baggage passes through the scanner. The X-ray source generates an X-ray beam that passes through and is partially attenuated by the baggage and is then received by the detector array. During each measuring interval the detector array generates data representative of the integral of density of the planar segment of the baggage through which the X-ray beam passes, and this data is used to form one or more raster lines of a two-dimensional image. As the conveyor belt transports the baggage past the stationary source and detector array, the scanner generates a two-dimensional image representative of the density of the baggage, as viewed by the stationary detector array. The density image is typically displayed for analysis by a human operator.

Techniques using dual energy X-ray sources are known for providing additional information about a material's characteristics, beyond solely a density measurement. Techniques using dual energy X-ray sources involve measuring the X-ray absorption characteristics of a material for two different energy levels of X-rays. Depending upon the calibration of the scanner, dual energy measurements provide an indication of dual parameters of the material being scanned. For example, at one calibration setting, the dual parameters can be chosen to be the material's effective atomic number (Z is denoted as "effective atomic number") and the material's density. At another calibration setting, the dual parameters can be chosen to be the material's photoelectric coefficients and the material's Compton coefficients. At yet another calibration setting, the dual parameters can be chosen to be an amount of a first material present (e.g., plastic) and an amount of a second material present (e.g., aluminum). Dual energy X-ray techniques for energy-selective reconstruction of X-ray Computer Tomography (hereinafter referred to as CT) images are described, for example, in Robert E. Alvarez and Albert Macovski, "Energy-selective Reconstructions in X-ray Computerized Tomography," Phys. Med. Biol. 1976, Vol. 21, No. 5, 733-744; and U.S. Pat. Nos. 4,029,963 and 5,132,998. One algorithm used to generate such dual parameters from dual energy X-ray projection data is known as the Alvarez/Macovski Algorithm (hereinafter referred to as AMA). Others are known in the art.

One proposed use for such dual energy techniques has been in connection with a baggage scanner for detecting the presence of explosives in baggage. Explosive materials are generally characterized by a known range of atomic numbers and are therefore amenable to detection by such dual energy X-ray sources. One such dual energy source is described in U.S. Pat. No. 5,661,774, entitled "Improved Dual Energy Power Supply," assigned to the present assignee and incorporated herein by reference. Other dual energy sources are known in the art.

Most explosives capable of significantly damaging an aircraft are sufficiently large in length, width, and height so as to be readily detectable by an X-ray scanner system regardless of the explosive's orientation within the baggage. Plastic explosives, however, present a particular challenge to baggage scanning systems. Due to their moldable nature, plastic explosives may be formed into geometric shapes that are difficult to detect. A plastic explosive powerful enough to damage an aircraft may be formed into a relatively thin sheet that is extremely small in one dimension and is relatively large in the other two dimensions. The detection of plastic explosives may be difficult because it may be difficult to see the explosive material in the image, particularly when the material is disposed so that the thin sheet is parallel to the direction of the X-ray beam as the sheet passes through the system.

Accordingly, a great deal of effort has been made to design a better baggage scanner. Such designs, for example, have been described in U.S. Pat. No. 4,759,047 (Donges et al.); U.S. Pat. No. 4,884,289 (Glockmann et al.); U.S. Pat. No. 5,132,988 (Tsutsui et al.); U.S. Pat. No. 5,182,764 (Peschmann et al.); U.S. Pat. No. 5,247,561 (Kotowski); U.S. Pat. No. 5,319,547 (Krug et al.); U.S. Pat. No. 5,367,552 (Peschmann et al.); U.S. Pat. No. 5,490,218 (Krug et al.) and German Offenlegungsschrift DE 31 503 06 A1 (Heimann GmbH).

At least one of these designs, described in U.S. Pat. No. 5,182,764 (Peschmann et al.) and U.S. Pat. No. 5,367,552 (Peschmann et al.) (hereinafter the '764 and '552 patents), has been commercially developed and is referred to hereinafter as the "Invision Machine." The Invision Machine includes a CT scanner of the third generation type, which typically includes an X-ray source and an X-ray detector system secured respectively to diametrically opposite sides of an annular-shaped platform or disk. The disk is rotatably mounted within a gantry support so that in operation the disk continuously rotates about a rotation axis while X-rays pass from the source through an object positioned within the opening of the disk to the detector system.

The detector system can include a linear array of detectors disposed as a single row in the shape of a circular arc having a center of curvature at the focal spot of the X-ray source, i.e., the point within the X-ray source from which the X-rays emanate. The X-ray source generates a fan shaped beam, or fan beam, of X-rays that emanates from the focal spot, passes through a planar imaging field, and is received by the detectors. The CT scanner includes a coordinate system defined by X-, Y- and Z-axes, wherein the axes intersect and are all normal to one another at the center of rotation of the disk as the disk rotates about the rotation axis. This center of rotation is commonly referred to as the "isocenter." The Z-axis is defined by the rotation axis and the X- and Y-axes are defined by and lie within the planar imaging field. The fan beam is thus defined as the volume of space defined between a point source, i.e., the focal spot, and the receiving surfaces of the detectors of the detector array exposed to the X-ray beam. Because the dimension of the receiving surfaces of the linear array of detectors is relatively small in the Z-axis direction the fan beam is designed to be relatively thin in the Z-axis direction. Each detector generates an output signal representative of the intensity of the X-rays incident on that detector. Since the X-rays are partially attenuated by all the mass in their path, the output signal generated by each detector is representative of the density of all the mass disposed in the imaging field between the X-ray source and that detector.

As the disk rotates, the detector array is periodically sampled, and for each measuring interval each of the detectors in the detector array generates an output signal representative of the density of a portion of the object being scanned during that interval. The collection of all of the output signals generated by all the detectors in a single row of the detector array for any measuring interval is referred to as a "projection," or equivalently as a "view," and the angular orientation of the disk (and the corresponding angular orientations of the X-ray source and the detector array) during generation of a projection is referred to as the "projection angle." At each projection angle, the path of the X-rays from the focal spot to each detector, called a "ray," increases in cross section from an appropriate point source to the receiving surface area of the detector, and thus is thought to magnify the density measurement because the receiving surface area of the detector area is larger than any cross sectional area of the object through which the ray passes.

As the disk rotates around the object being scanned, the scanner generates a plurality of projections at a corresponding plurality of projection angles. Using well-known algorithms, a CT image of the object may be generated from all the projection data collected at each of the projection angles. The CT image is representative of the density of a two dimensional "slice" of the object through which the fan beam has passed during the rotation of the disk through the various projection angles. The resolution of the CT image is determined in part by the width of the receiving surface area of each detector in the plane of the fan beam, the width of the detector being defined herein as the dimension measured in the same direction as the width of the fan beam, while the length of the detector is defined herein as the dimension measured in a direction normal to the fan beam parallel to the rotation or Z-axis of the scanner. In general, the resolution of the CT image is inversely proportional to the width of the receiving surface of each detector in the plane of the fan beam.

Figure 1:
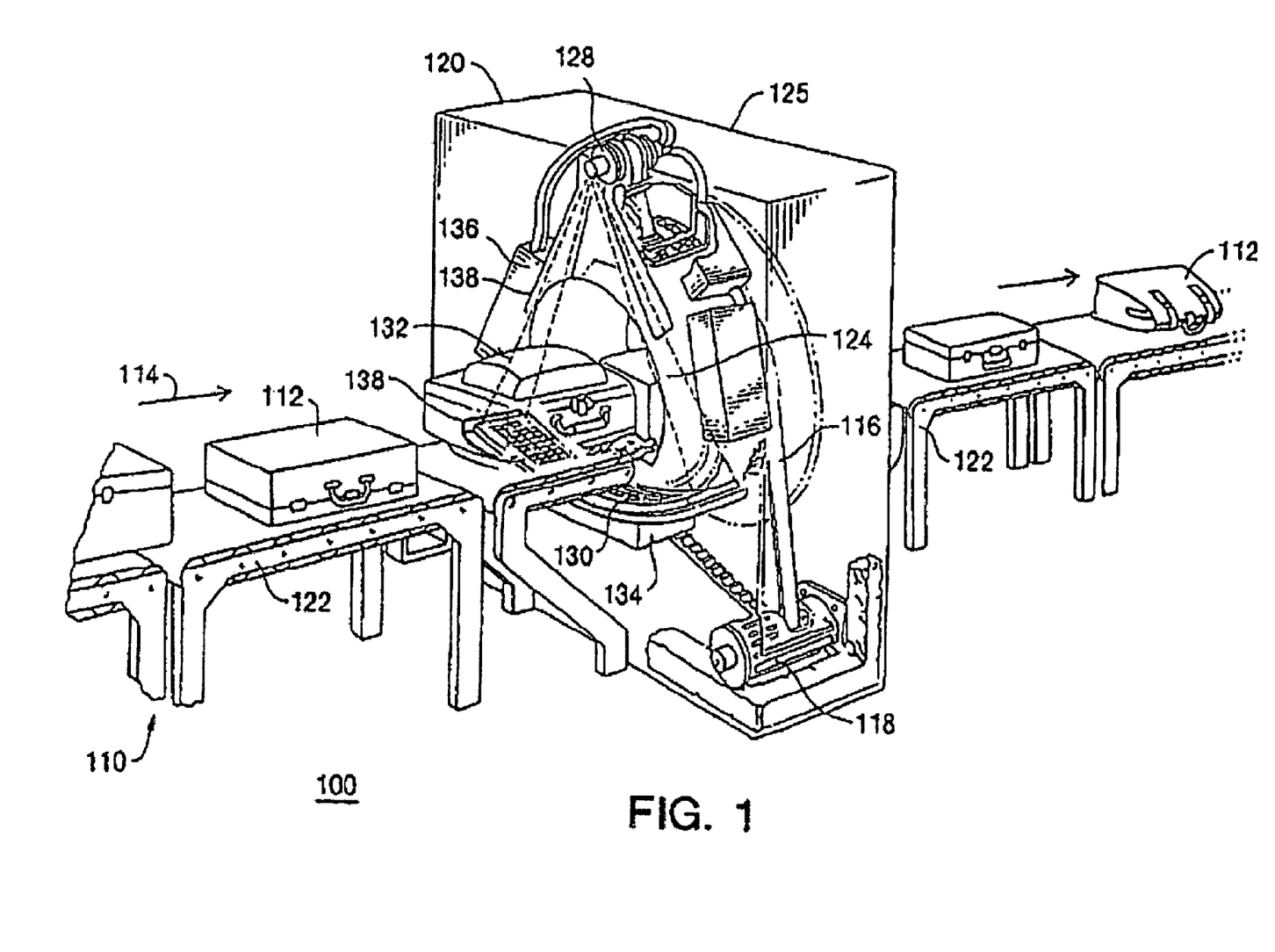
FIG. 1 is a perspective view of a baggage scanning system, known in the prior art, and which can be adapted to incorporate the system and perform method described herein.
Figure 2:
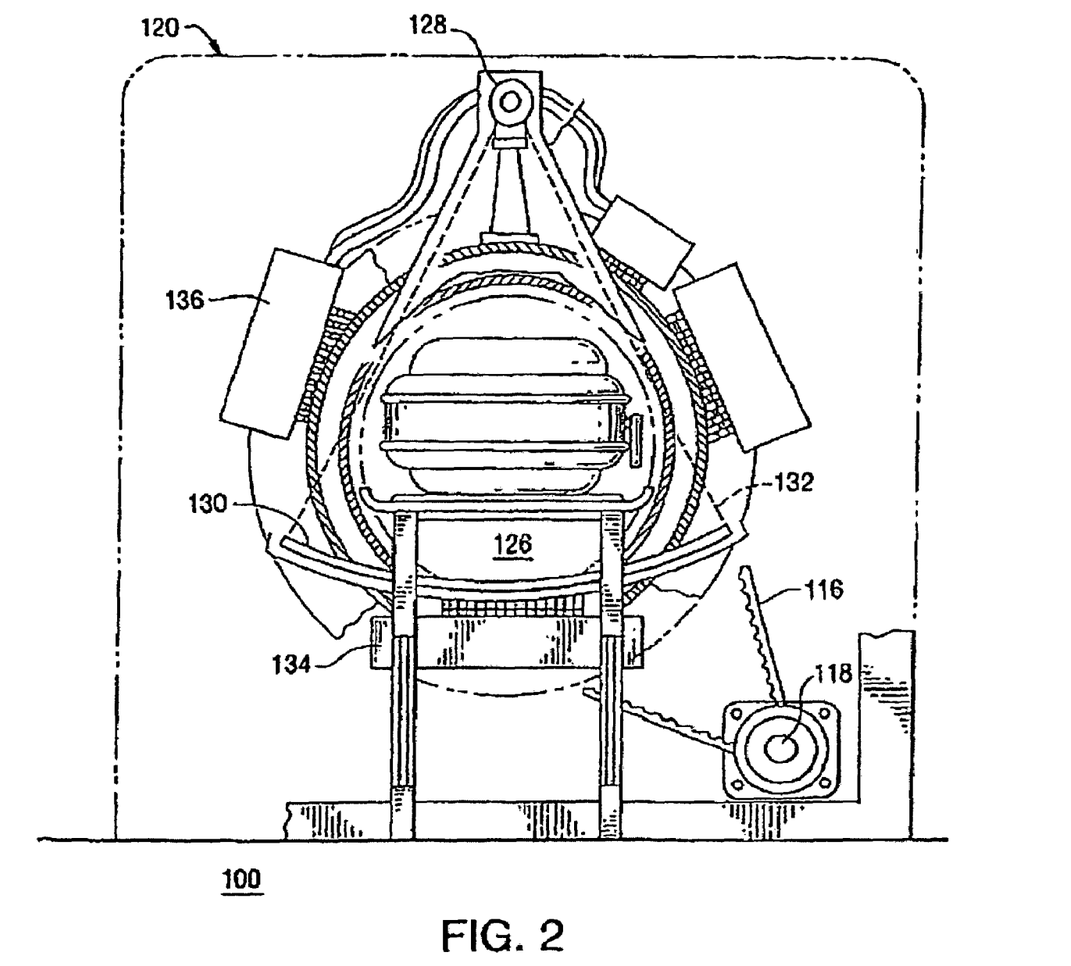
FIG. 2 is a cross-sectional end view of the system of FIG. 1.
Figure 3:
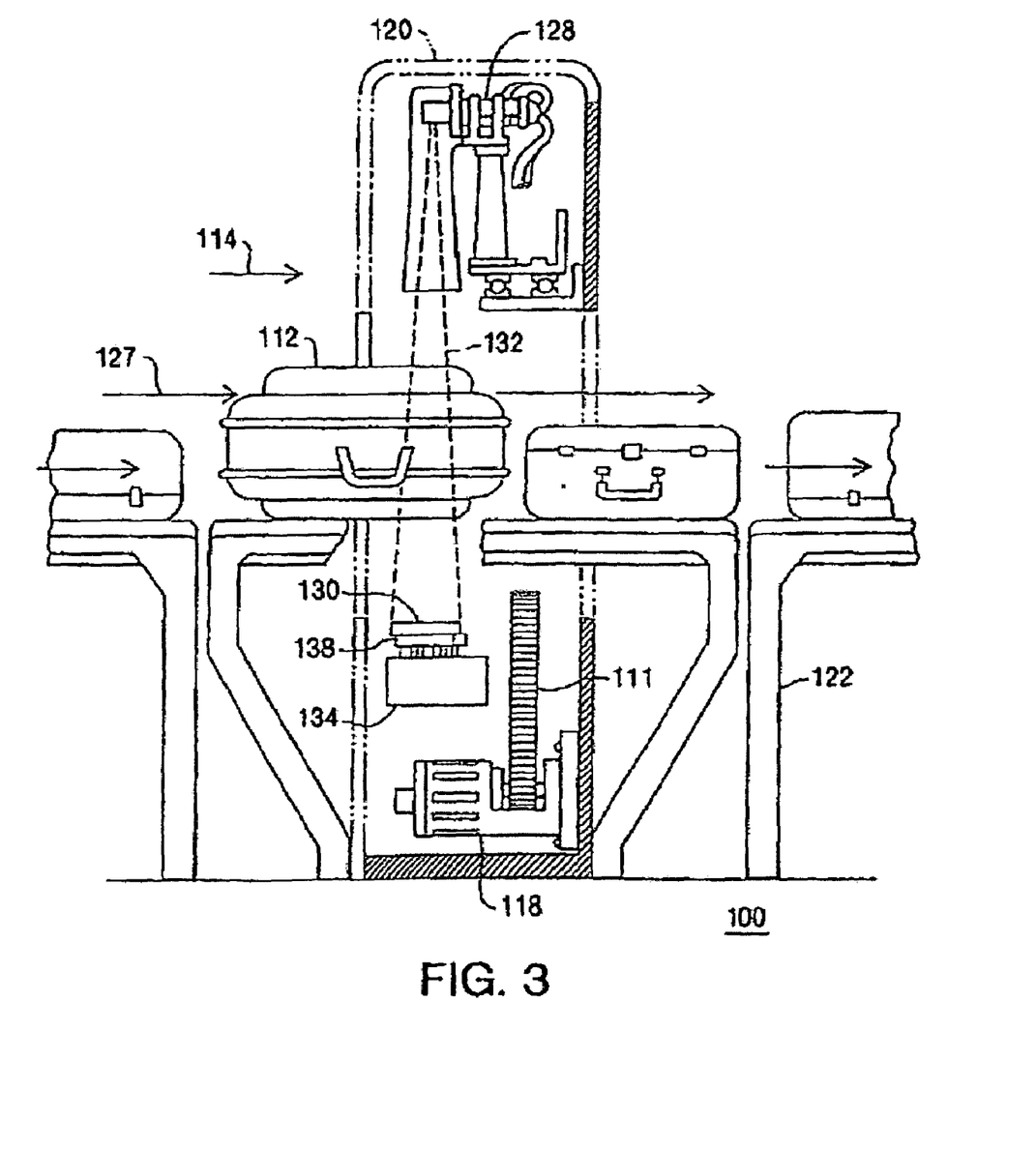
FIG. 3 is a cross-sectional radial view of the system of FIG. 1.

Referring to the drawings, FIGS. 1, 2 and 3 show perspective, end cross-sectional and radial cross-sectional views, respectively, of a typical baggage scanning system 100, which includes a conveyor system 110 for continuously conveying baggage or luggage 112 in a direction indicated by arrow 114 through a central aperture of a CT scanning system 120. The conveyor system includes motor driven belts for supporting the baggage. Conveyer system 110 is illustrated as including a plurality of individual conveyor sections 122; however, other forms of conveyor systems may be used.

The CT scanning system 120 includes an annular shaped rotating platform, or disk, 124 disposed within a gantry support 125 for rotation about a rotation axis 127 (shown in FIG. 3) that is preferably parallel to the direction of travel 114 of the baggage 112. Disk 124 is driven about rotation axis 127 by any suitable drive mechanism, such as a belt 116 and motor drive system 118, or other suitable drive mechanism, such as the one described in U.S. Pat. No. 5,473,657 issued Dec. 5, 1995 to Gilbert McKenna, entitled "X-ray Tomographic Scanning System," which is assigned to the present assignee and, which is incorporated herein in its entirety by reference. Rotating platform 124 defines a central aperture 126 through which conveyor system 110 transports the baggage 112.

The system 120 includes an X-ray tube 128 and a detector array 130 which are disposed on diametrically opposite sides of the platform 124. The detector array 130 is preferably a two-dimensional array, such as the array described in U.S. Pat. No. 6,091,795 entitled, "Area Detector Array for Computed Tomography Scanning System." Other suitable arrays are known in the art. The system 120 further includes a data acquisition system (DAS) 134 for receiving and processing signals generated by detector array 130, and an X-ray tube control system 136 for supplying power to, and otherwise controlling the operation of, X-ray tube 128. The system 120 is also preferably provided with a computerized system (not shown) for processing the output of the data acquisition system 134 and for generating the necessary signals for operating and controlling the system 120. The computerized system can also include a monitor for displaying information including generated images. System 120 also includes shields 138, which may be fabricated from lead, for example, for preventing radiation from propagating beyond gantry 125.

The X-ray tube 128 may generate a pyramidally shaped beam, often referred to as a "cone beam," 132 of X-rays that pass through a three dimensional imaging field, through which conveying system 110 transports baggage 112. After passing through the baggage disposed in the imaging field, detector array 130 receives cone beam 132 and generates signals representative of the densities of exposed portions of baggage 112. The beam therefore defines a scanning volume of space. Platform 124 rotates about its rotation axis 127, thereby transporting X-ray source 128 and detector array 130 in circular trajectories about baggage 112 as the conveyor system 110 continuously transports baggage through central aperture 126, so as to generate a plurality of projections at a corresponding plurality of projection angles. When dual energy scanning mode is configured, the control system 136 supplies modulated high voltages with respect to alternating projection angles to the X-ray tube 128. The detector array 130 then receives data corresponding to high-energy and low-energy X-ray spectra in alternating projection angles.

Figure 4:
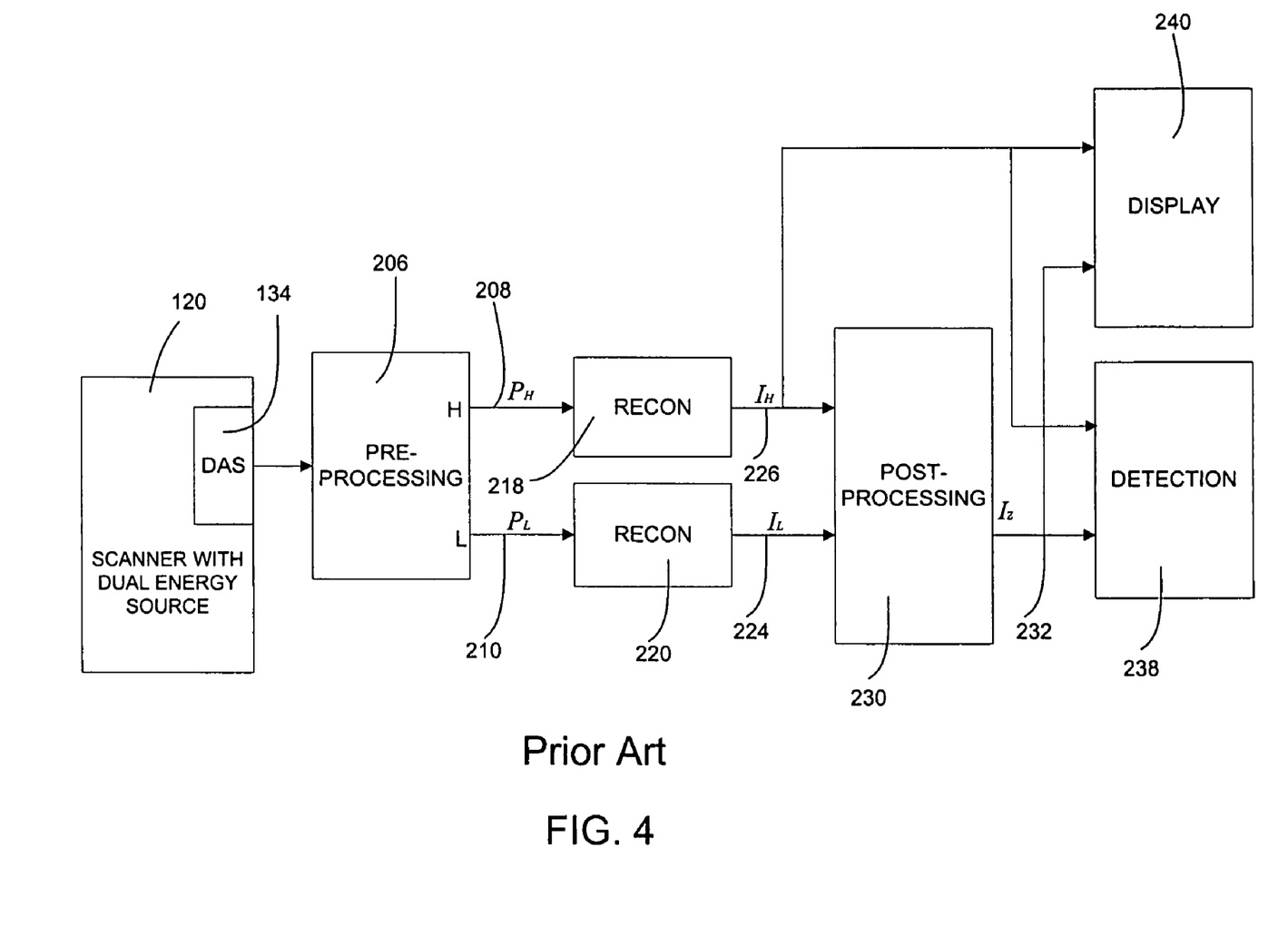
FIG. 4 is a signal flow block diagram of a prior art system capable of performing post-reconstruction analysis, useful in the system of FIG. 1.

Post-reconstruction analysis and pre-reconstruction analysis are the two prior art techniques generally recognized for using dual energy X-ray sources in materials analysis (e.g., in a baggage scanner for detecting the presence of explosives in baggage). In post-reconstruction analysis, the signal flow is as shown in FIG. 4. The scanner 120 is typically similar to the one shown in FIGS. 1-3 and has an X-ray source capable of producing a fan or cone beam at two distinct energy levels (i.e., dual energy). The DAS 134 gathers signals generated by detector array 130 at discrete angular positions of the rotating platform 124, and passes the signals to the pre-processing unit 206. The pre-processing unit 206 re-sorts the data it receives from the DAS 134 in order to optimize the sequence for the subsequent mathematical processing. The pre-processing unit 206 also corrects the data from the DAS 134 for detector temperature, intensity of the primary beam, gain and offset, and other deterministic errors. Finally, the pre-processing unit 206 extracts data corresponding to high-energy views and routes it to a high-energy path 208, and routes the data corresponding to low-energy views to a low-energy path 210. A first reconstruction computer 218 receives the projection data from the high-energy path 208 and generates a CT image $I_H$ 226 corresponding to the high-energy series of projections. A second reconstruction computer 220 receives the projection data from the low-energy path 210 and generates a CT image $I_L$ 224 corresponding to the low-energy series of projections. A post-processing unit 230 receives the high-energy CT image 226 and the low-energy CT image 224 and performs voxel-by-voxel processing to yield the effective atomic number (Z is denoted as effective atomic number) image $I_z$ 232. The Z image 232 and the high-energy CT image 226 can be provided to operators on a display 240, and both images can be used for automatic explosive detection in 238 as well. The images from the post-reconstruction analysis usually do not yield accurate estimates of the material's effective atomic number, and suffer low SNR (Signal to Noise Ratio) and many artifacts as well.

Figure 5:
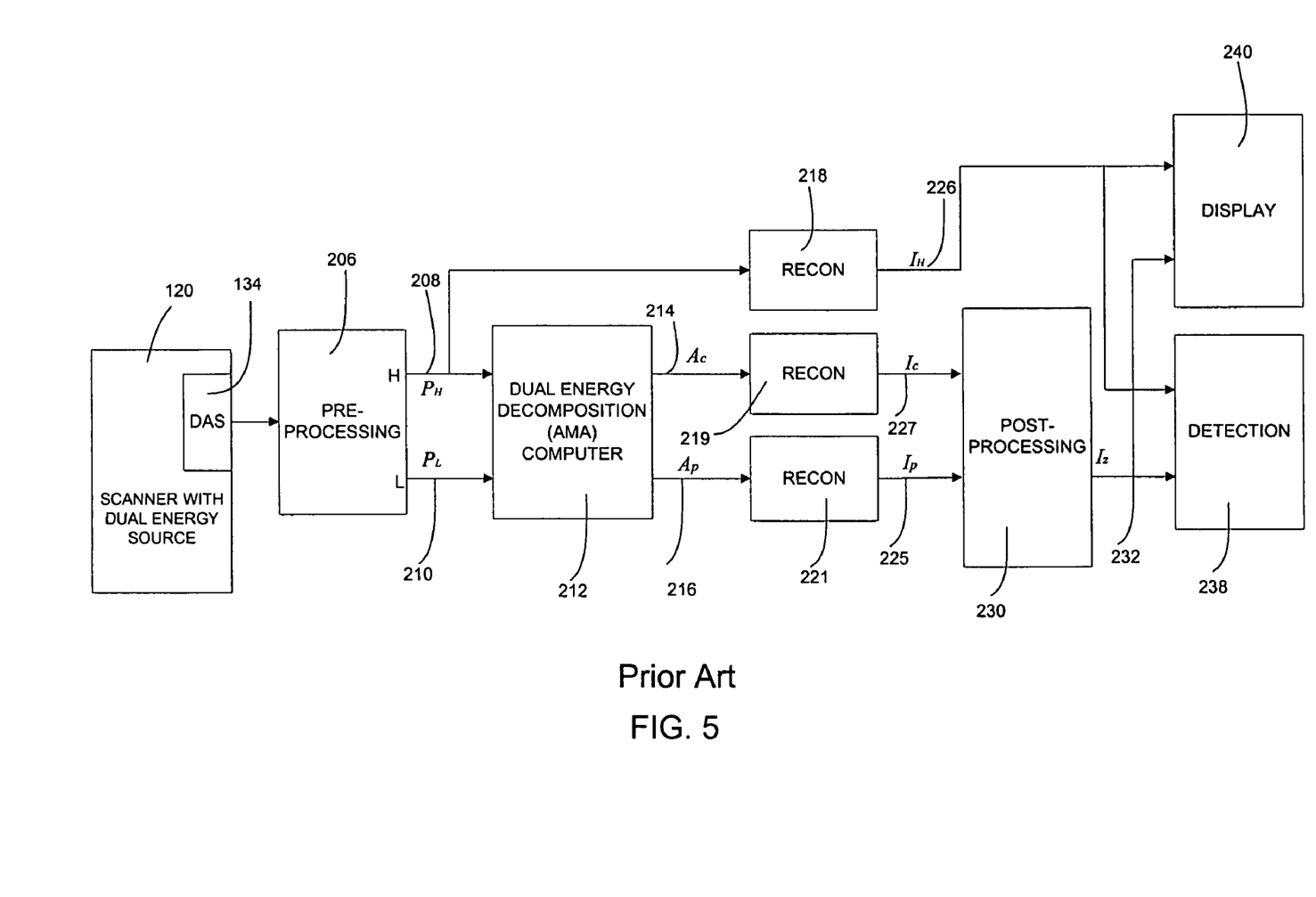
FIG. 5 is a signal flow block diagram of a prior art system capable of performing pre-reconstruction analysis, useful in the system of FIG. 1.

In pre-reconstruction analysis, the signal flow is as shown in FIG. 5. As is described herein for pre-reconstruction analysis, the dual energy decomposition computer 212 receives the projection data on the high-energy path 208 and the low-energy path 210 and performs the Alvarez/Macovski Algorithm to produce a first stream of projection data $A_c$ 214, which is dependent on a first parameter of the material being scanned, and a second stream of projection data $A_p$ 216, which is dependent on a second parameter of the material scanned. The first material parameter is often the Compton coefficient $a_c$, and the second material parameter is often the photoelectric coefficient $a_p$. A first reconstruction computer 219 receives the first stream of projection data 214 and generates a Compton image $I_c$ 227 from the series of projections corresponding to the first material parameter. A second reconstruction computer 221 receives the second stream of projection data 216 and generates a photoelectric image $I_p$ 225 from the series projections corresponding to the second material parameter. The third reconstruction computer 218 receives the stream of projection data 208 and generates a high-energy CT image $I_H$ 226. The two images 225 and 227 are processed in the post-processing unit 230 to yield a Z image $I_z$ 232. The High-energy CT image 226 and the Z image 232 can be provided to operators on a display 240, and both images can be used for automatic explosive detection in detection unit 238 as well. The pre-reconstruction analysis yields better estimates of material's effective atomic number than the post-reconstruction analysis. However the pre-reconstruction analysis requires one more reconstruction computer than the post-reconstruction analysis.

Various approaches have been used for decomposition of the input projection data $P_L$ and $P_H$ into Compton projections $A_c$ and photoelectric projections $A_p$. For example, the AMA method approximates $P_L$ and $P_H$ using polynomial functions in terms of $A_c$ and $A_p$. The coefficients of the polynomial functions are determined through a calibration procedure as follows. By measuring the projection values of the combination of various thicknesses of two known materials, the coefficients can be calculated through a polynomial least squares fitting between the measured and modeled $P_L$ and $P_H$. Once the coefficients of the polynomial functions are determined, the decomposition of the Compton and Photoelectric projections $A_c$ and $A_p$ from projections $P_L$ and $P_H$ is usually solved using the Newton-Raphson method.

Another prior art method of performing decomposition is the direct approximation method, discussed in L. A. Lehmann, R. E. Alvarez, A. Macovski, W. R. Brody, N. J. Pelc, S. J. Riederer, and A. L. Hall, *Generalized Image Combinations In Dual KVP Digital Radiography*, Med. Phys. 8, 659-667 (1981). In the direct approximation method, $A_c$ and $A_p$ are approximated as polynomial functions in terms of $P_L$ and $P_H$. The coefficients of the polynomial functions in the direct approximation method are determined through a calibration procedure by measuring the projection values of the combination of various thicknesses of two known materials.

In yet another prior art method, decomposition is accomplished using iso-transmission lines, described K. Chuang and H. K. Huang, *A Fast Dual-Energy Computational Method Using Isotransmission Lines and Tables*, Med. Phys. 14, 186-192 (1987). According to this method, for a given projection value, an isotransmission line is represented by a linear equation in two basis functions. The isotransmission line method requires a large amount of calibration data. Further, the isotransmission line becomes increasingly non-linear as the projection value increases. In such a situation, the linear equations are not valid and the method causes large approximation errors.

CT images and Z (effective atomic number) images can be generated from both the pre-reconstruction and post-reconstruction analysis. The CT images measure the CT number at each image pixel of scanned materials, which approximates the density of the materials; and the Z image measures the effective atomic number at each image pixel of the scanned materials. The measurements of both CT number and Z are used for automatic explosive detection.

An automatic detection algorithm can be used on the CT and Z images to detect prohibited items, such as explosives, as described in "Computed tomography apparatus and method for classifying objects" invented by Simanovsky, et. al. (U.S. Pat. No. 6,317,509). Since the automatic explosive detection yields certain percentage of false alarms, operators are required to intervene to resolve the falsely alarmed baggage. It is very labor intensive to open the baggage and perform hand search, therefore, it is desirable to display the images generated by the CT scanner in combination with the automatic explosive detection results on some 3D display devices, such as "Volumetric three-dimensional display system" invented by Dorval, et. al. (U.S. Pat. No. 6,554,430), or on 2D LCD or CRT displays with 3D volume rendering, such as "Volume rendering techniques for general purpose graphics hardware" by Christof Rezk-Salama in Ph. D. Dissertation at University of Erlangen in December 2001.

In order to resolve whether a piece of baggage on screen has produced a false detection, operators may need to have access to different display modes to see different aspects of the baggage to make a good decision. Such display modes can include turning on/off a color on the screen representing metal parts of the baggage, turning on/off a color representing a threat object, removing metal parts of the baggage on screen, etc. However, changing from one display mode to another is not necessarily easily and quickly accomplished. Further, color rendering may make it difficult to see threat objects displayed within the scanned baggage, and therefore difficult to determine whether one is dealing with a false alarm, or a true threat. It is desirable to have a display device that can change one display mode to another quickly so that operators can use visual parallax to obtain more information about the baggage from the display to make correct decision.

Further, dual energy CT scanners are usually capable of generating at least two types of images, such as CT images and Z images, and the automatic explosive detection system also generates at least one type of result images, such as a label image indicating the detection result. These images cannot be simultaneously provided as inputs into a 3D display device or a 3D volume render for displaying, which usually require an image containing RGBA information of each voxel. RGB represents the color of each voxel of the image (Red, Green, and Blue components), and A (Alpha) represents the transparency of the voxel.

SUMMARY OF THE DISCLOSURE

In accordance with one aspect of the disclosed method, volumetric multi-energy CT images, including a CT image, a Z image, and a label image are displayed from an automatic explosive detection, wherein the total number of bits of the CT image, the Z image, and the label image per voxel is N. The method comprises (a) generating an index image, of which each voxel has M bits, through a nonlinear transformation of the CT image, the Z image, and the label image, wherein M is less than N; (b) rotating and coloring the index image as desired; and (c) rendering and displaying the rotated and colored index image. In one embodiment, the coloring is performed after rotating the index image is performed. In one embodiment, coloring includes (a) generating an RGBA look-up-table corresponding to the selected display mode, and (b) applying the RGBA look-up-table to the rotated index image.

In accordance with one aspect of the disclosed system, volumetric multi-energy CT images, including a CT image, a Z image, and a label image are displayed from an automatic explosive detection, wherein the total number of bits of the CT image, the Z image, and the label image per voxel is N. The system comprises (a) a module arranged and configured so as to generate an index image, of which each voxel is represented by M bits, through a nonlinear transformation of the CT image, the Z image, and the label image, wherein M is less than N; (b) a module arranged and configured so as to allow rotation and coloring of the index image; and (c) a module arranged and constructed so as to render and display the rotated and colored image.

In accordance with one aspect of the disclosure, a preferred system for and method of displaying multi-energy CT images from the CT projection data acquired by scanning a set of objects using at least two x-ray spectra, wherein the projection data includes a set of low energy projections and a set of high energy projections, is disclosed. The dual energy CT scanner generates at least two 3D volumetric images, preferably one as a CT image, and the other as a Z (effective atomic number) image. The automatic explosive detection system preferably generates a label image indicating the detection result. Finally, the CT image, Z image, and the label image are preferably used to generate an index image for display. In one embodiment, each voxel of the index image has less number of bits than the total number of bits of the corresponding voxels of the CT image, Z image, and label image.

In accordance with one aspect of the disclosure, the CT image is used to display the content of the scanned objects. In another embodiment, the index image includes a metal bit derived from the CT image and Z image indicating the metal property of the voxel. More than one bit in the index image can be used to reflect more information of the metal, such as light metal, or heavy metal.

In accordance with one aspect of the disclosure, rotational angles determined by an operator are fed into a video card for interpolating the index image. In another embodiment, window and level parameters for displaying the CT image are also input from the operator. Given the rotational angle, and the window and level parameters, an RGBA look-up-table is generated corresponding to a display mode selected by an operator. A list of pre-defined display modes is also preferably provided in accordance with one aspect of the disclosed system and method. In another embodiment, the generation of RGBA look-up tables includes at least two parameters: window and level. The change of the window value and level value may require recalculation of the RGBA look-up tables.

The interpolated image is preferably converted to an RGBA image using the generated RGBA look-up table (provided, for example) in a graphics card of the scanner display system, and rendered into a 2D projection image to an LCD panel for display.

In accordance with one aspect of the disclosure, a system for displaying volumetric multi-energy CT images is also provided, wherein a CT image, a Z (effective atomic number) image, and a label image from an automatic explosive detection system are provided. The system preferably includes modules configured to implement the above functionality. In one embodiment, the system may include a module for generating an index image from the CT image, the Z image, and the label image. In one embodiment the system may include a module for generating RGBA look-up tables corresponding to different display modes.

While this disclosure has been particularly shown and described with references to preferred embodiments thereof, it will be understood by those skilled in the art that various changes in form and details may be made therein without departing from the spirit and scope of the disclosure as defined by the following claims.

BRIEF DESCRIPTION OF THE DRAWINGS

The drawing figures depict preferred embodiments by way of example, not by way of limitations. In the figures, like reference numerals refer to the same or similar elements.

DETAILED DESCRIPTION OF THE PREFERRED EMBODIMENTS

In accordance with at least one aspect of the present disclosure, a method and system are provided for displaying volumetric multi-energy CT images from the CT projection data acquired by scanning a set of objects using at least two x-ray spectra, wherein the projection data includes a set of low energy projections and a set of high energy projections. In one preferred embodiment, the method first generates a CT image and a Z (atomic number) image. An automatic explosive detection system generates a label image from the CT image and the Z image. A nonlinear transformation is then performed to transform the CT image, the Z image, and the label image into an index image for display, in which the number of bits per voxel is less than the total number of bits per voxel of the CT image, Z image, and label image. The index image is then loaded into the video memory of the display device once. Orientation angle for the luggage to be displayed on the screen input from an operator is used to interpolate the index image. A look-up-table is also generated corresponding to a display mode, which is selected from a list of pre-defined display modes by an operator. The look-up-table provides a means for coloring each voxel of the interpolated index image at a given rotational angle. Rendering the colored interpolated index image into a 2D display, for example, on a LCD panel, is finally performed. When an operator changes a display mode, a new look-up-table is generated. The above process is repeated to render (or display) the image. Since the size of the look-up-table is much smaller than the already bit-reduced index image, the provided algorithm yields instant (e.g., less than 10 milliseconds) response to the change of the display mode by an operator.

Figure 6:
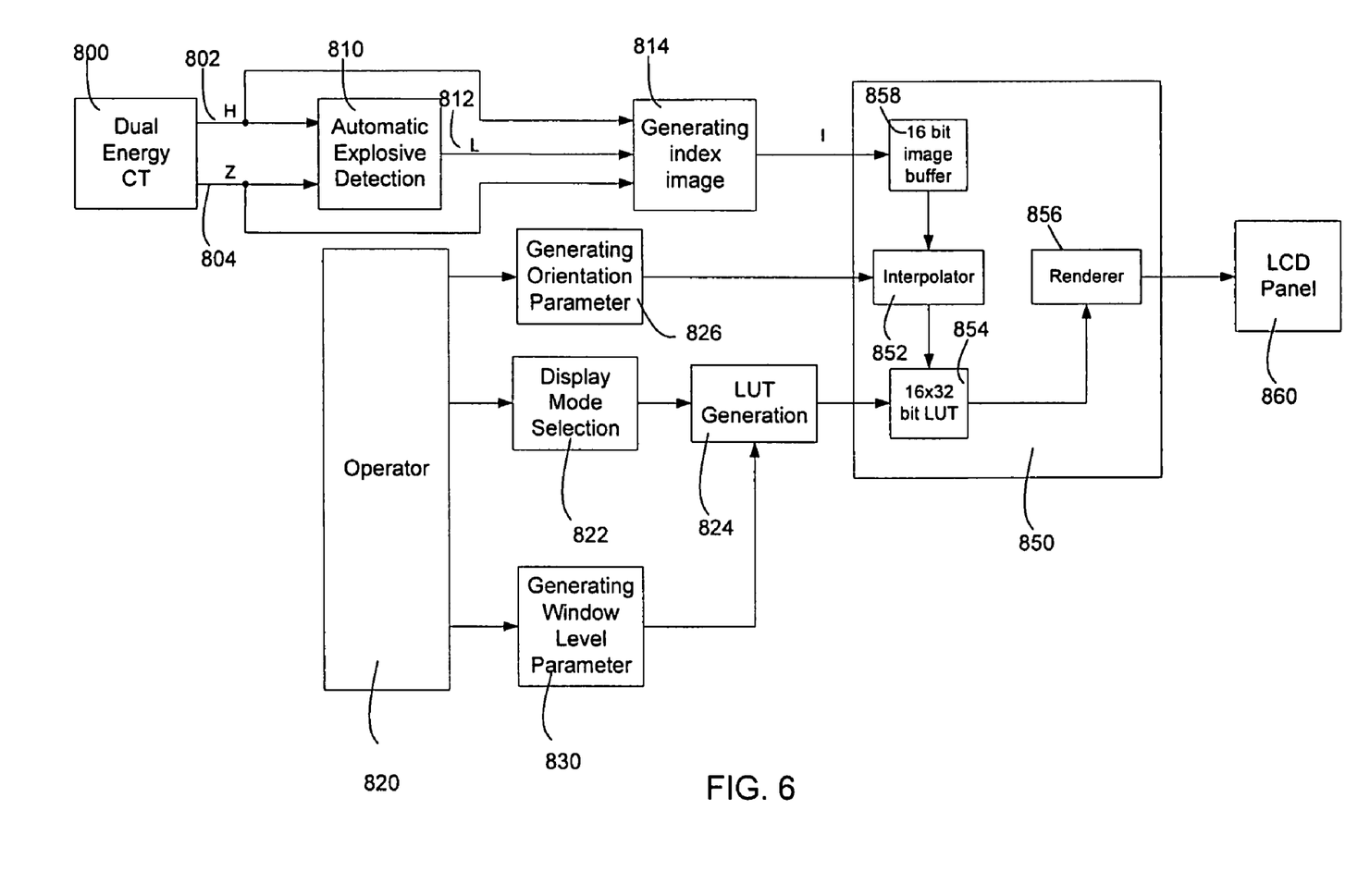
FIG. 6 contains a flow block diagram which illustrates the logical flow of one embodiment of a system for displaying 3D volumetric multi-energy CT images with automatic explosive detection results in accordance with one of the aspects of the present disclosure

FIG. 6 contains a flow diagram which illustrates the logical flow of one embodiment for displaying 3D volumetric multi-energy CT images with automatic explosive detection results of the present disclosure. The dual energy CT scanner 800 generates a 3D volumetric CT image data H 802 and a 3D volumetric Z (effective atomic number) image data Z 804. The generation of the CT image data and Z image data from a dual energy CT scanner uses methods described in the assignee's "Method of and system for adaptive scatter correction in multi-energy computed tomography" by Zhengrong Ying, et al. U.S. application Ser. No. 10,853,942, filed on May 26, 2004; incorporated herein by reference; "Method of and system for destreaking the photoelectric image in multi-energy computed tomography" by Zhengrong Ying, et. al. U.S. application Ser. No. 10/860,984, filed on Jun. 4, 2004; incorporated herein by reference; "Decomposition of Multi-Energy Scan Projections using Multi-Step Fitting" by Naidu, et. al. U.S. application Ser. No. 10/611,572, filed on Jul. 1, 2003, incorporated herein by reference; "Method of and system for computing effective atomic number image in multi-energy computed tomography" by Zhengrong Ying, et. al. U.S. application Ser. No. 10/850,910, filed on May 21, 2004; incorporated herein by reference; and "Method of and system for X-ray spectral correction in multi-energy computed tomography," invented by Ram Naidu, et. Al. U.S. application Ser. No. 10/899,775, filed on Jul. 27, 2004; incorporated herein by reference.

The CT image data H comprises data representing a plurality of voxels, each of which represents a density measurement of scanned objects; for example, water has a physical density of 1 g/cc, and the CT image of water has value of 1000 Hounsfield Unit (HU). The effective atomic number image Z also comprises a plural of voxels, each of which represents an effective atomic number measurement of scanned objects; for example, aluminum has atomic number of 13, and the Z image of aluminum has value of 1300 Z Unit (ZU).

The CT image data H 802 and the Z image data Z 804 are applied to the input of an automatic explosive detection unit 810. The automatic explosive detection unit uses methods described in the assignee's "Apparatus and Method for Eroding Objects in Computed Tomography Data," invented by Sergey Simanovsky, et al., U.S. application Ser. No. 09/021,781, filed on Feb. 11, 1998, now U.S. Pat. No. 6,075,871, issued on Jun. 13, 2000, incorporated herein by reference; "Apparatus and Method for Combining Related Objects in Computed Tomography Data," invented by Ibrahim M. Bechwati, et al., U.S. application Ser. No. 09/022,060, filed on Feb. 11, 1998, now U.S. Pat. No. 6,128,365, issued on Oct. 3, 2000, incorporated herein by reference; "Apparatus and Method for Detecting Sheet Objects in Computed Tomography Data," invented by Sergey Simanovsky, et al., U.S. application Ser. No. 09/022,165, filed on Feb. 11, 1998, now U.S. Pat. No. 6,025,143, issued on Feb. 15, 2000, incorporated herein by reference; "Apparatus and Method for Classifying Objects in Computed Tomography Data Using Density Dependent Mass Thresholds," invented by Ibrahim M. Bechwati, et al., U.S. application Ser. No. 09/021,782, filed on Feb. 11, 1998, now U.S. Pat. No. 6,076,400, issued on Jun. 20, 2000, incorporated herein by reference. The automatic explosive detection unit 810 generates data representing a label image L, in which all the voxels of a detected threat are assigned a same unique positive integer number. For example, if there are three detected threats in a piece of baggage, the corresponding label image will have labels from 1 to 3 indicating the first, second, and the third threat object; the voxels of the first object are all assigned a label 1 in the label image, and so on.

The unit 814 takes the CT image data H, the atomic number image data Z, and the label image data L, and generates data representing an index image. The details of generating the display image from data representing the CT image, Z image, and label image are described below. Each CT number in the CT image H is represented by a 16-bit number as follows, $$H = h_{15}h_{14}\ldots h_1h_0$$

where, $h_i$ is a binary valued number. Thus, the CT number of a voxel ranges from 0 to 65535, inclusive.

Each atomic number value in the Z image is also represented by a 16-bit number as follows, $$Z = z_{15}z_{14}\ldots z_1z_0$$

Thus, each Z number also ranges from 0 to 65536. The label image L comprises the labels of the detected threats, and it is also represented by a 16-bit number as follows, $$L = l_{15}l_{14}\ldots l_1l_0$$

The index image I contains the information from the CT image H, the Z image Z, and the label image L. Current graphics cards can support data representing index image I usually up to 16 bits for each datum, and is represented as follows, $$I = i_{15}i_{14}\ldots i_1i_0$$

Thus, each voxel of each of the three images is represented by a 16-bit number. In order to integrate the three images with total of 48 bits at each voxel into one index image with total of 16 bit, the following nonlinear transformation scheme is preferably used to distribute the bits for the three images: 8 bits $i_7i_6\ldots i_1i_0$ for the CT image, 1 bit $i_8$ for metal voxel derived using the CT image and the Z image, and 7 bits $i_{15}i_{14}\ldots i_{10}i_9$ for the label image. The details of such an assignment are described below.

Converting the 16-bit CT image into the 8 bits of the index image, denoted as $I_h$, is performed as follows, $$I_h = i_7i_6\ldots i_1i_0 = \begin{cases} h_{11}h_{10}\ldots h_5h_4 & \text{if } h_{15}h_{14}h_{13}h_{12} = 0 \\ 11\ldots 11 & \text{if } h_{15}h_{14}h_{13}h_{12} > 0 \end{cases}$$

In the above operation, the CT number greater than $2^{12}-1=4095$ is saturated at $2^{12}-1=4095$.

The metal bit $i_8$ of the index image, denoted also as $I_m$, is obtained as follows, $$I_m = i_8 = \begin{cases} 1 & \text{if } H \geq 2200 \text{ or } Z \geq 1300 \\ 0 & \text{otherwise} \end{cases}$$

Converting the 16-bit label image into the 7 bits of the index image, denoted as $I_l$, is performed as follows, $$I_l = i_{15}i_{14}\ldots i_{10}i_9 = \begin{cases} l_6l_5\ldots l_1l_0 & \text{if } l_{15}l_{14}\ldots l_8l_7 = 0 \\ 11\ldots 11 & \text{if } l_{15}l_{14}\ldots l_8l_7 > 0 \end{cases}$$

The generated 16-bit index image is then sent to the 16-bit image buffer 858 of the graphics card 850, such as XFX GEFORCE ULTRA 6800 graphics card. The interpolator 852 of the graphics card 850 takes the orientation parameter generated by unit 826 commanded from the operator 820 and the 16 bit index image to generate an interpolated index image. The orientation parameters comprise three rotational angles of the baggage, and can be obtained from an input device, such as a keyboard by an operator.

The operator 820 selects one display mode from a predefined list of display modes in unit 822, and these display modes include linear Alpha transfer function mode, triangular Alpha transfer function mode, grayscale mode, metal color mode, potential threat color mode, threat color mode, threat color toggling mode, etc.

Window w and level l are two parameters for displaying the image. Only the CT numbers within the range between $$l - \frac{w}{2}$$

and $$l + \frac{w}{2}$$

are being displayed. The window w and level l are also chosen by operator 820 through unit 830, and fed into LUT generation unit 824.

Given the selected display mode and the window and level parameters, LUT generation unit 824 generates a corresponding RGBA look-up-table. There are 8 bits for each of RGBA channel, i.e., the numbers for these channels range from 0 to 255. In the following, examples of the RGBA look-up-tables corresponding to different display modes are described in detail.

The following transfer functions for Alpha A are used:

Linear: in this mode, the opacity A is linearly mapped from the CT number of each voxel within the specified window and level; the higher the CT number is, the more opaque the voxel is.

$$A = \begin{cases} \left\lfloor \frac{255\left[I_h - \left(l - \frac{w}{2}\right)\right]}{w} + 0.5 \right\rfloor, & \text{if } l - \frac{w}{2} \leq I_h \leq l + \frac{w}{2} \\ 0, & \text{otherwise} \end{cases}$$

where $\lfloor x \rfloor$ is the largest integer not greater than x, .

Triangular: in this mode, the most opaque voxel is the voxel with the CT number equal to the level value; the higher or lower the CT number is, the more transparent the voxel is.

$$A = \begin{cases} \left\lfloor \dfrac{510\left[I_h - \left(l - \dfrac{w}{2}\right)\right]}{w} + 0.5 \right\rfloor, & \text{if } l - \dfrac{w}{2} \le I_h \le l \\ \left\lfloor \dfrac{510[l - I_h]}{w} + 255.5 \right\rfloor, & \text{if } l \le I_h \le l + \dfrac{w}{2} \\ 0, & \text{otherwise} \end{cases}$$

Note that it is important to set the Alpha value to zero for outside the window and level range in display.

The following describes different transfer functions for the RGB channels. These transfer functions are used in combination with the Alpha transfer function. The transfer functions can be described in the following three categories: grayscale, partial color, and full color.

In the grayscale mode, the following transfer function is used for the RGB channels:

$$R = G = B = \begin{cases} \left\lfloor \dfrac{255\left[I_h - \left(l - \dfrac{w}{2}\right)\right]}{w} + 0.5 \right\rfloor, & \text{if } l - \dfrac{w}{2} \le I_h \le l + \dfrac{w}{2} \\ 0, & \text{otherwise} \end{cases}$$

The transfer functions of the partial color modes including metal mode, potential threat mode, threat mode are as follows, Metal mode: in this mode, the metal voxels are colored in blue or green depending on the voxel being part of the threats or not.

$$R = \begin{cases} \left\lfloor \dfrac{255\left[I_h - \left(l - \dfrac{w}{2}\right)\right]}{w} + 0.5 \right\rfloor, & I_m = 0 \\ 0, & I_m = 1 \end{cases}$$

$$G = \begin{cases} \left\lfloor \dfrac{255\left[I_h - \left(l - \dfrac{w}{2}\right)\right]}{w} + 0.5 \right\rfloor, & I_m = 1, I_l > 0, \text{ or } I_m = 0 \\ 0, & I_m = 1, I_l = 0 \end{cases}$$

$$B = \begin{cases} \left\lfloor \dfrac{255\left[I_h - \left(l - \dfrac{w}{2}\right)\right]}{w} + 0.5 \right\rfloor, & I_m = 1, I_l = 0, \text{ or } I_m = 0 \\ 0, & I_m = 1, I_l > 0 \end{cases}$$

Potential threat mode: in this mode, the voxels within certain CT number range are colored in orange.

$$R = \left\lfloor \dfrac{255\left[I_h - \left(l - \dfrac{w}{2}\right)\right]}{w} + 0.5 \right\rfloor$$

$$G = \begin{cases} 0, & I_l = 0, I_m = 0, \\ & 600 \le I_h \le 1800 \text{ or } I_l > 0 \\ \left\lfloor \dfrac{255\left[I_h - \left(l - \dfrac{w}{2}\right)\right]}{w} + 0.5 \right\rfloor, & \text{otherwise} \end{cases}$$

$$B = \left\lfloor \dfrac{255\left[I_h - \left(l - \dfrac{w}{2}\right)\right]}{w} + 0.5 \right\rfloor$$

Threat mode: in this mode, the current selected threat object is colored red, and the next threats are colored yellow. The current threat object can be toggled among all the detected threats. Denoting $i_c$ as the current selected threat object, the threat mode has the following described RGB transfer function, $$R = \left\lfloor \dfrac{255\left[I_h - \left(l - \dfrac{w}{2}\right)\right]}{w} + 0.5 \right\rfloor;$$

$$G = \begin{cases} 0, & I_l = i_c \\ \left\lfloor \dfrac{255\left[I_h - \left(l - \dfrac{w}{2}\right)\right]}{w} + 0.5 \right\rfloor, & \text{otherwise} \end{cases};$$

$$B = \begin{cases} 0, & I_l > 0 \\ \left\lfloor \dfrac{255\left[I_h - \left(l - \dfrac{w}{2}\right)\right]}{w} + 0.5 \right\rfloor, & \text{otherwise} \end{cases}$$

The above partial color modes can be used in any combinations. For example, when metal color, potential threat color, and threat color are all turned on, this corresponds to a full color mode; metal color and threat color can be turned on, but the potential color is turned off.

The table look-up unit 854 of the graphics card 850 takes the interpolated index image and the RGBA table, and outputs a colored interpolated 3D image to the renderer 856. Common methods for rendering a 3D image into a 2D projection image can be found in the literature, such as in "Volume rendering techniques for general purpose graphics hardware" by Christof Rezk-Salama in Ph. D. dissertation of University of Erlangen in December 2001. The rendered projection image is then output to an LCD panel 860 for display to the operator for on-screen threat resolution.

While this disclosure has been particularly shown and described with references to preferred embodiments thereof, it will be understood by those skilled in the art that various changes in form and details may be made therein without departing from the spirit and scope of the disclosure as defined by the following claims. Such variations include combining two or more display modes into a new display mode and changing the order of interpolating for rotation and coloring the index image.

The invention claimed is:

1. A scanner for (a) scanning objects and generating a plurality of volumetric multi-energy CT images and a label image representing detected results from a threat detection system, each image being represented by a number of voxels, with each voxel of each image being represented by a predetermined number of bits representing information associated with the voxel of that image, and for (b) displaying each of the multi-energy CT images and label image as a result of scanning objects and using a threat detection system, comprising:
   a processor configured so as to:
   a. combine, for each voxel, the bits representing the voxel for all of the CT images and label image so as to create a combined set of voxels each of N bits representing information included in the voxel for all of the CT images and label image; and
   b. nonlinearly transform, for each combined voxel, the N bits to M bits representing the corresponding voxel in an index image, wherein M<N, and wherein the index image contains sufficient information for separately displaying each CT image and label image.

2. A scanner according to claim 1, further including a threat detection system.

3. A scanner according to claim 1, wherein the processor includes a graphics processor unit (GPU), and wherein the index image information can be loaded into the GPU once for displaying any one or more of the CT images and label image.

4. A scanner according to claim 1, wherein the processor is further configured to generate the processed information corresponding to the index image so that the CT images and label image can be displayed all from the index image.

5. A scanner according to claim 1, wherein the processor is further configured to color and rotate the index image as desired.

6. A scanner according to claim 3, further including a display configured so that the index image and each of the rotated and colored images can be displayed.

7. A scanner according to claim 1, wherein the scanner is used for explosive detection, and the CT images are a CT density image, an atomic number (Z) image and a label image representing the explosive detection results.

8. A scanner according to claim 1, wherein the CT images are multi-energy images acquired using at least two x-ray spectra for generating at least two 3D volumetric images.

9. A scanner according to claim 1, wherein at least one of the M bits representing each voxel of the index image is indicative of a metal property of the volume represented by the voxel.

10. A scanner according to claim 1, wherein the processor includes a graphics processor unit (GPU) and the GPU is configured to interpolate the index image.

11. A scanner according to claim 1, wherein the processor is further configured to rotate and color the index image in response to an operator's manipulation.

12. A method of (a) scanning objects and generating a plurality of volumetric multi-energy CT images and a label image representing detected results from a threat detection system, each image being represented by a number of voxels, each defined by a predetermined number of bits representing information associated with the voxel for each image, and (b) displaying multi-energy CT images and label images as a result of scanning objects and using a threat detection system, comprising:

for each voxel, combining the bits for all of the CT images and label image so as to create N bits of a combined voxel representing information included in that voxel for all of the CT images and label image; and for each combined voxel, nonlinearly transforming the N bits to M bits representing index image information, wherein M<N, and wherein the index image contains sufficient information for separately displaying each CT image and label image.

13. A method according to claim 12, further including generating the plurality of volumetric multi-energy CT images and label image from a threat detection system.

14. A method according to claim 12, further including loading the index image information into a graphics processor unit (GPU) once so that any one or more of the volumetric CT images and label image can be processed for display.

15. A method according to claim 12, further including generating the processed information corresponding to the index image so that the CT images and label image can be displayed all from the index image.

16. A method according to claim 12, further including coloring and rotating the index image as desired.

17. A method according to claim 16, displaying each of the rotated and colored index images.

18. A method according to claim 12, further including scanning each object for explosives, wherein the CT images are a CT density image, an atomic number (Z) image and a label image representing the explosive detection results.

19. A method according to claim 12, wherein the CT images are multi-energy images acquired using at least two x-ray spectra for generating at least two 3D volumetric images.

20. A method according to claim 12, wherein at least one of the M bits representing each voxel of the index image is indicative of a metal property of the volume represented by the voxel.

21. A method according to claim 12, further including interpolating the index image using a graphics processor unit in order to rotate the image.

22. A method according to claim 11, further including rotating and coloring the index image in response to an operator's manipulation.

* * * * *